(12) United States Patent
Melander et al.

(10) Patent No.: US 9,833,574 B2
(45) Date of Patent: Dec. 5, 2017

(54) SPRING-LOADED INJECTION DEVICE WITH AN INJECTION BUTTON

(71) Applicant: Novo Nordisk A/S, Bagsvaerd (DK)

(72) Inventors: Matias Melander, Copenhagen (DK); Mikkel Avlund, Soeborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 408 days.

(21) Appl. No.: 14/422,395

(22) PCT Filed: Aug. 19, 2013

(86) PCT No.: PCT/EP2013/067256
§ 371 (c)(1),
(2) Date: Feb. 19, 2015

(87) PCT Pub. No.: WO2014/029745
PCT Pub. Date: Feb. 27, 2014

(65) Prior Publication Data
US 2015/0202369 A1   Jul. 23, 2015

Related U.S. Application Data

(60) Provisional application No. 61/691,347, filed on Aug. 21, 2012.

(30) Foreign Application Priority Data

Aug. 20, 2012   (EP) .................................... 12181035

(51) Int. Cl.
*A61M 5/24*   (2006.01)
*A61M 5/20*   (2006.01)
*A61M 5/315*   (2006.01)

(52) U.S. Cl.
CPC ................ *A61M 5/24* (2013.01); *A61M 5/20* (2013.01); *A61M 5/2033* (2013.01);
(Continued)

(58) Field of Classification Search
CPC .......... A61M 5/31525; A61M 5/31551; A61M 5/31571; A61M 5/3158; A61M 5/24;
(Continued)

(56) References Cited

U.S. PATENT DOCUMENTS

| 5,320,609 A | 6/1994 | Haber et al. |
| 5,928,202 A | 7/1999 | Linnebjerg |
| 2009/0048561 A1 | 2/2009 | Burren et al. |

FOREIGN PATENT DOCUMENTS

| CN | 101005868 A | 7/2007 |
| CN | 101014378 A | 8/2007 |

(Continued)

*Primary Examiner* — Nathan R Price
*Assistant Examiner* — Courtney Fredrickson
(74) *Attorney, Agent, or Firm* — Wesley Nicolas

(57) ABSTRACT

The present invention relates to a spring-loaded medical injection device for automatically ejecting set doses of a drug having an injection button (10). The injection device comprises a housing having a dose setting member (20) for straining an injection spring when setting the size of the dose to be injected and a release element (30) for releasing the strained injection spring to eject the set dose. The injection button (10) is movable in a distal direction against the bias of a return spring (1) and movable in a proximal direction by the force of the return spring (1). Further, the injection button (10) moves with it the release element from a first position to a second position. The release element (30) is further coupled to the injection button (10) by a plurality of fingers (31, 15) which disengages the injection button (10) from the release element (30) in the first position and engages the injection button (10) with the release element (30) in the second position, such that the injection button (10) can move a distance axially independently of the release element (30) in the first position and the injection button (10) and the release element (30) move axially together in the second position.

10 Claims, 3 Drawing Sheets

(52) U.S. Cl.
CPC .... *A61M 5/31525* (2013.01); *A61M 5/31551* (2013.01); *A61M 5/3158* (2013.01); *A61M 5/31571* (2013.01); *A61M 5/31585* (2013.01); *A61M 5/31593* (2013.01); *A61M 2005/202* (2013.01); *A61M 2005/2407* (2013.01); *A61M 2005/2481* (2013.01)

(58) Field of Classification Search
CPC ............ A61M 5/3155; A61M 5/31593; A61M 5/2033; A61M 2005/2481; A61M 2005/2407
See application file for complete search history.

(56) References Cited

FOREIGN PATENT DOCUMENTS

| | | |
|---|---|---|
| CN | 101022841 A | 8/2007 |
| CN | 101678167 A | 3/2010 |
| EP | 594357 A1 | 4/1994 |
| JP | 2009519788 A | 5/2009 |
| WO | 2006076921 A1 | 7/2006 |
| WO | 2007071080 A1 | 6/2007 |
| WO | 2008031235 A1 | 3/2008 |
| WO | 2009092807 A1 | 7/2009 |

# SPRING-LOADED INJECTION DEVICE WITH AN INJECTION BUTTON

CROSS-REFERENCE TO RELATED APPLICATIONS

This application is a 35 U.S.C. §371 National Stage application of International Application PCT/EP2013/067256 (published as WO2014/029745), filed Aug. 19, 2013, which claims priority to European Patent Application 12181035.2, filed Aug. 20, 2012; this application claims priority under 35 U.S.C. §119 to U.S. Provisional Application 61/691,347, filed Aug. 21, 2012.

THE TECHNICAL FIELD OF THE INVENTION

The invention relates to the release mechanism of an automatic spring driven injection device. The invention especially relates to the coupling of the injection button with the release element and more especially to a mechanism allowing the injection button to engage and disengage the release element in dependency of its axial position.

DESCRIPTION OF RELATED ART

An automatic spring driven injection device is disclosed in WO 2006/076921. FIG. 10 discloses an embodiment in which a tube-like release member is coupled to a proximally located injection button which a user can push in the distal direction with the tip of a finger against the bias of a return spring encompassed between the housing and the injection button. A rotational dose setting button for setting the size of the dose to be ejected is coupled to the housing. When setting the size of the dose the user further torsionally strains an injection spring. Once a dose is set, it can be ejected by the operation of the proximally located injection button. When a user pushes the injection button in the distal direction, the distal end of the release tube moves the drive member out of its engagement with the housing such that the injection spring is free to drive the piston rod forward and thereby eject the set dose. When the user removes his finger from the injection button the return spring encompassed between the housing and the injection button lifts the injection button and the release tube in the proximal direction whereby the drive member re-engages the housing preventing the injection spring in ejecting more drug from the cartridge.

An injection button for a manual injection device is disclosed in EP 594,357. This injection button has a plurality of resilient legs integrally moulded with the remaining part of the injection button such that the injection button is lifted back to its initial position once a user removes his finger from the injection button.

Further, a coupling system for a push rod and a piston in a medical syringe is disclosed in U.S. Pat. No. 5,928,202. In this system a plurality of resilient fingers are deflected inwardly when the fingers are moved into a channel.

WO 2007/071080 and WO 2008/031235 discloses solutions similar to the one disclosed in WO 2006/076921 wherein a return spring urges the injection button in the proximal direction once the user removes his finger from the injection button.

When a user removes his finger from the injection button in the embodiment disclosed in FIG. 10 of WO 2006/076921 it is important that the drive member quickly re-engages with the housing to prevent further ejection.

However, tolerances are usually present in the connection between the injection button and the release tube. Further tolerances in the spring could also be present. The result of these tolerances is that when the return spring is most compressed (which is during injection) and the user removes his finger from the injection button, the initial force of the spring is used first to lift the injection button which at the end of the tolerance string then engages the release tube to lift this thus re-engaging the driver. As a result, and depending upon the tolerances, only a limited spring force is available to lift the release tube which is a major disadvantage as it is the lifting of the release tube that allows the re-engagement of the drive member with the housing to prevent further ejection. In order for the user to e.g. properly pause the injection it is very important that the re-engagement occurs swift and accurate once the finger is removed from the injection button.

DESCRIPTION OF THE INVENTION

It is an object of the present invention to provide a spring driven injection device for multiple automatic injections of set doses in which the spring force returning the injection button and the release element is distributed such that proper re-engagement of the drive member is guaranteed independently of the tolerances thus e.g. making it possible to utilize a return spring with no pretension such as e.g. a polymeric spring.

The invention is defined in claim 1.

Accordingly, in one aspect of the present invention, an injection device for a spring driven injection of a liquid drug is provided, which injection device comprises:

A housing making up an outer shell. The housing usually holds the cartridge containing the drug and the mechanical component making up the dose setting and injection mechanism.

A dose setting member coupled to housing by which dose setting member a user can strain an injection spring which could be a torsion spring in which a torque is stored without none or only very limited axial compression.

An injection button by which an injection can be performed by activation of the injection button, usually by the user applying an axial pressure on the button during injection and wherein a return spring returns the injection button to its initial position when no pressure is applied.

Further, a release element is provided which can operate between a first position and a second position.

The release element is releasable coupled to the injection button via a plurality of radially working fingers. The fingers are provided either integral with the release element or integral with the injection button.

In the first position, the fingers are in a disengaging position wherein the dose setting button is disengaged from the release element. The dose setting button is thus able to move an axial distance independently of the release element.

In the second position, the fingers are moved to an engaging position which couples the injection button to the release member. The second position is preferably the position in which the return spring urges the dose setting button and the release element together in the proximal direction.

The release element is the element in the mechanical construction that directly or indirectly releases the injection spring to perform the injection e.g. as disclosed in WO 2006/076921, which is hereby incorporated in the present application by reference.

The release element is not necessarily directly connected to the injection spring but can be coupled to the injection spring via a mechanism that releases the injection spring upon activation of the release element.

One function of the invention is that the injection button can move a distance axially independently of the release element in the first position and that the injection button and the release element move axially together in the second position.

In this way it is secured that the largest force of the return spring when it is most compressed is used first to re-engage the release mechanism, and that a minor part of the spring force thereafter, as the return spring approaches its most extended state, is used to only lift the injection button independently of the release mechanism. In this way the largest force is available for re-engaging the release element with the housing when stopping or pausing the injection.

A part of the release element and a part of the injection button is guided in a channel having a fixed diameter. The channel is preferably provided in either the dose setting member or in the housing.

One of the two elements; the release element or the injection button is provided with the plurality of fingers. The outside diameter formed by the outer edges of these fingers is preferably larger than the diameter of the channel such that the fingers are squeezed radially when moved axially inside the channel.

This radial movement of fingers defines the boundaries between the first position and the second position. In the first position with the fingers outside the channel, the fingers are in their disengaged position whereas when the fingers are squeezed inside the channel, the release element is in its second position.

Thus in the second position, the release element and the injection button move axially together in a stiff connection whereas in the first position the two elements are decoupled.

The fingers are preferably provided with inwardly pointing means that engage behind a ridge provided on the injection button to thereby engage the injection button in the second position, however in case the fingers are provided on the injection button, the ridge or track could be provided on the release element itself.

The return spring which is usually not prestrained is preferably, but not exclusively, made from a suitable polymeric material and can be moulded as an integral part of either the injection button or the dose setting member (or alternatively as a part of the housing). However, alternatively an ordinary metallic compression spring is also usable.

Further, it is notable that the return spring need not be in physical abutment with the injection button, since due to the present invention, the initial movement of the return spring upon release of the injection button is transferred directly to lifting the release element.

DEFINITIONS

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle cannula in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Using the term "Automatic" in conjunction with an injection device means that, the injection device is able to perform the injection without the user of the injection device delivering the force needed to expel the drug. The force is typically delivered by an electric motor or by a spring as herein described which spring is usually strained by the user during dose setting. Such springs are usually prestrained with a certain force in order to avoid problems of delivering very small doses. Alternatively, the spring can be preloaded by the manufacturer with a preload sufficient to empty the full drug cartridge though a number of doses. Typically the user activates a latch or a button on the injection device to release the force accumulated in the spring when carrying out the injection.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as the relative dimensions are intended to serve illustrative purposes only.

Figure 1:
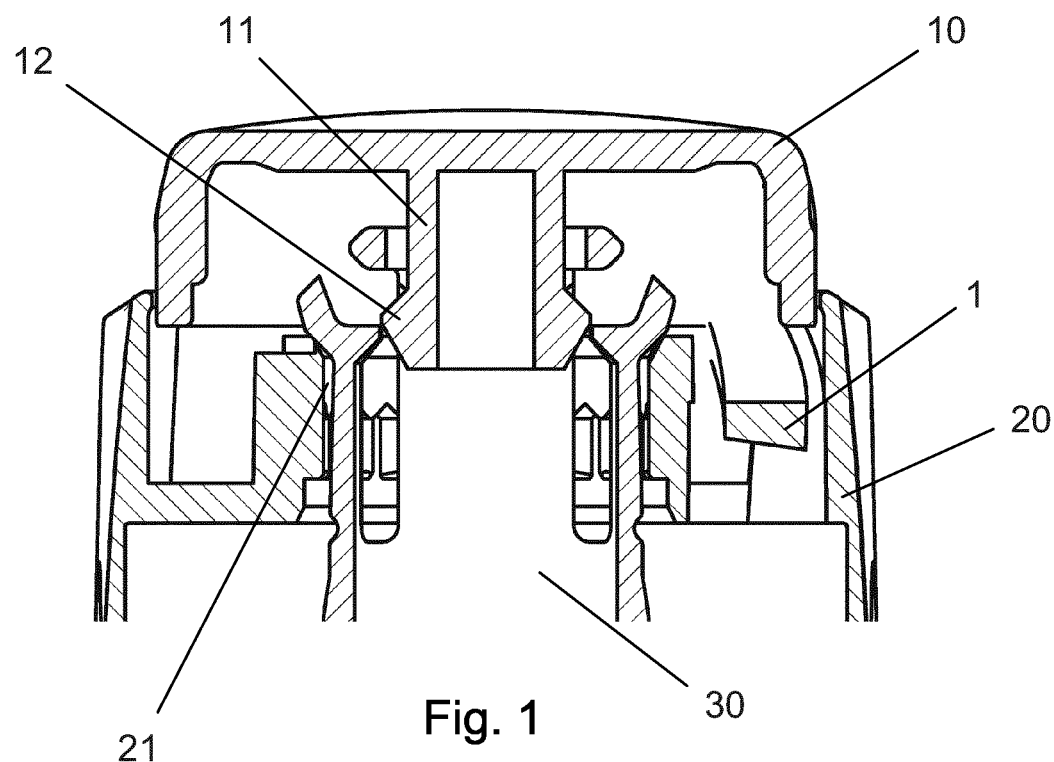
FIG. 1 show a cross sectional view of the release mechanism with no pressure applied.

In that context it may be convenient to define that the term "distal end" in the appended figures is meant to refer to the end of the injection device which usually carries the injection needle whereas the term "proximal end" is meant to refer to the opposite end pointing away from the injection needle and carrying the injection button as depictured in FIG. 1.

FIG. 1 to FIG. 6 discloses the release mechanism of an automatic spring driven injection device.

The embodiment disclosed in the FIGS. 1 to 5 depictures the release mechanism. An injection button 10 is provided at the proximal end of the injection device. As shown in FIG. 10 of WO 2006/076921, the injection button 10 is axially guided by the dose setting button 20 which again is rotatable coupled to the housing.

A release tube 30 is centrally located in the injection device. At its distal end this release tube 30 operates the mechanism releasing the injection spring to eject a set dose via a driver. An example of such mechanism is disclosed in FIG. 10 of WO 2006/076921.

A return spring 1 is encompassed between the dose setting button 20 and the injection button 20 urging the injection button 10 in the proximal direction. The return spring 1 is preferably moulded from a polymeric material.

In the first embodiment (FIG. 1-5), the injection button 10 is internally provided with a centrally located protrusion 11 which at its distal end has a radial ridge 12.

The release tube 30 is provided with a plurality of fingers 31. Only finger 31 actually needs to be flexible, the remaining fingers 31 could be formed as a rigid support structure. These fingers 31 extends through a channel 21 provided in the dose setting button 20. However, the channel 21 could alternatively be provided in the housing (not shown) or anywhere suitable. The fingers 31 are proximally provided with an outwardly pointing extension 32 which defines an outer diameter larger than the internal diameter of the channel 21 defined by the inner wall 22.

Figure 2:
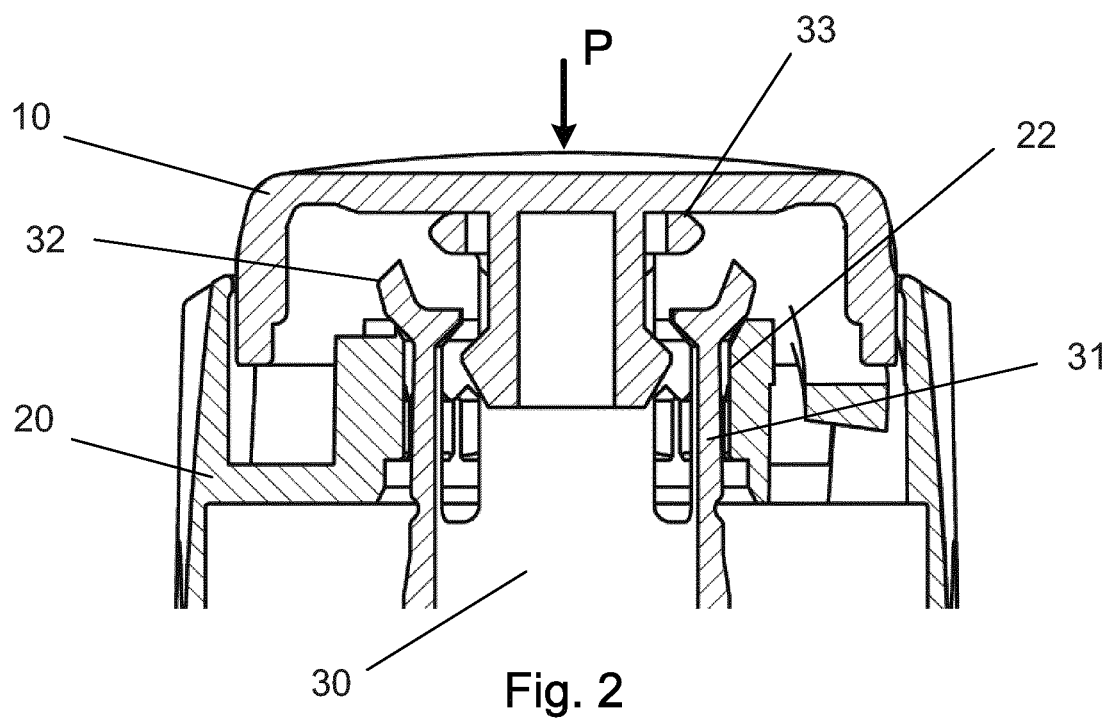
FIG. 2 show a cross sectional view of the release mechanism at the beginning of the injection.
Figure 3:
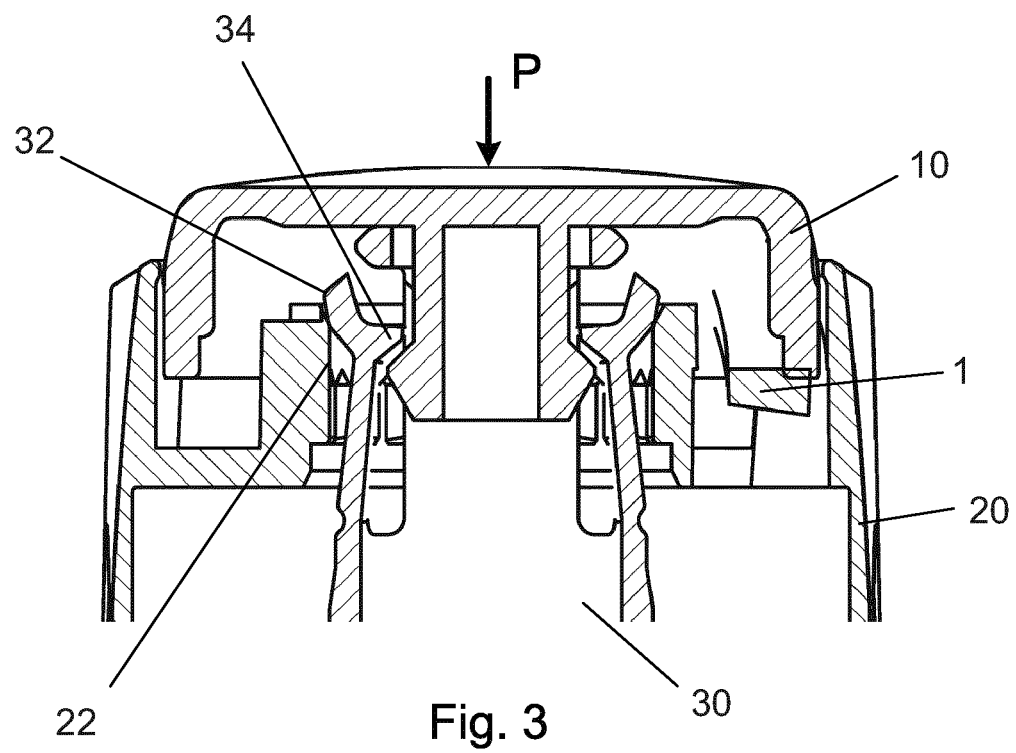
FIG. 3 show a cross sectional view of the release mechanism as the release tube engages with the dose setting button.

When a user applies an axial pressure (P) onto the injection button 10 during injection as depictured in FIG. 2, the injection button 10 first moves distally until it engages the most proximal end 33 of the release tube 30. Thereafter, as disclosed in FIG. 3, the release tube 30 moves together with the injection button 10 in the distal direction.

Figure 4:
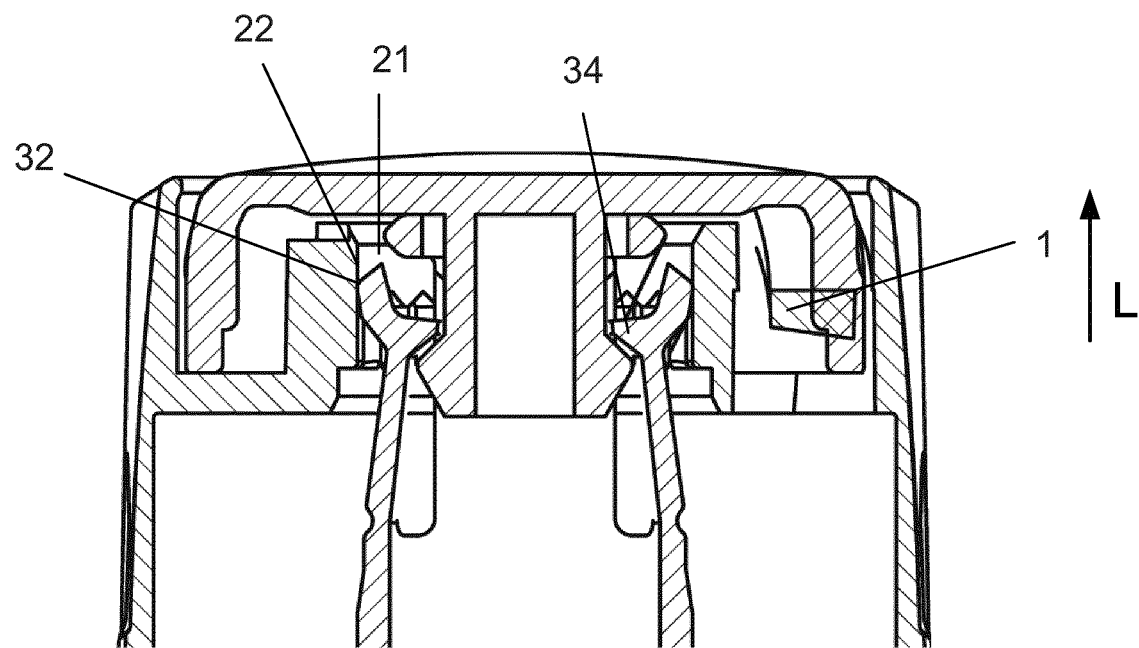
FIG. 4 show a cross sectional view of the release mechanism with the injection button fully depressed.
Figure 5:
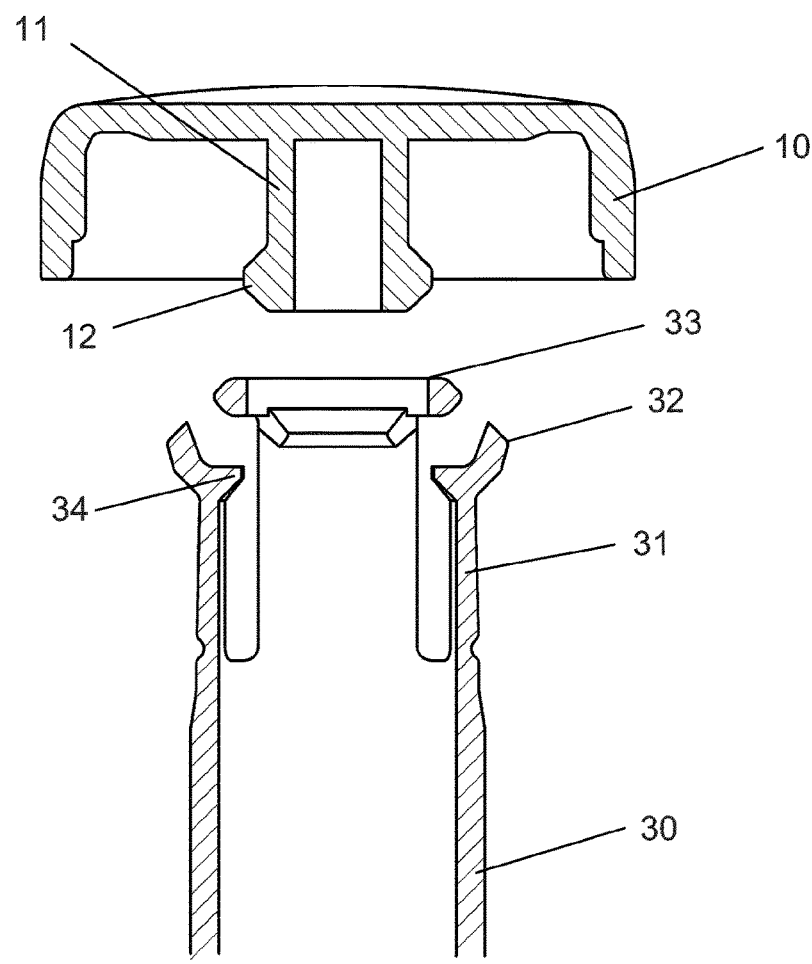
FIG. 5 show an exploded view of the release mechanism.

As the release tube 30 is moved distally the outer edge 32 on the fingers 31 abuts the internal wall 22 of the channel 21 and the fingers 31 are thus deflected inwardly as disclosed in FIG. 4.

Internally the release tube 30 is provided with a number of radially inwardly pointing knobs 34 which engages the protrusion 11 of the injection button 10 proximal to the radial ridge 12 as the protrusion 11 and the release tube 30 travels distally down into the channel 21.

When the user removes his finger from the injection button 10 so that no pressure is applied, the return spring 1 will start to lift the injection button 10 as indicated by the arrow L in FIG. 4. Since the injection button 10 in this position is locked to the release tube 30 due to the engagement between the ridge 12 and the knob 34, the largest force of the return spring 1, when it is most compressed, will be transferred to the release tube 30, such that a reengagement between the drive member and the housing is secured.

When the release mechanism is released, the outer edge 32 has reached a position above the opening of the channel 21 (as in FIG. 3) and the remaining force of the return spring 1 is used to move the injection button 10 independently of the release tube 30 until it reaches its initial position.

Should the last force of the return spring 1 be inadequate to lift the injection button 10 the last part of the way this will not influence the release mechanism, as the release tube 30 has already been lifted.

Figure 6:
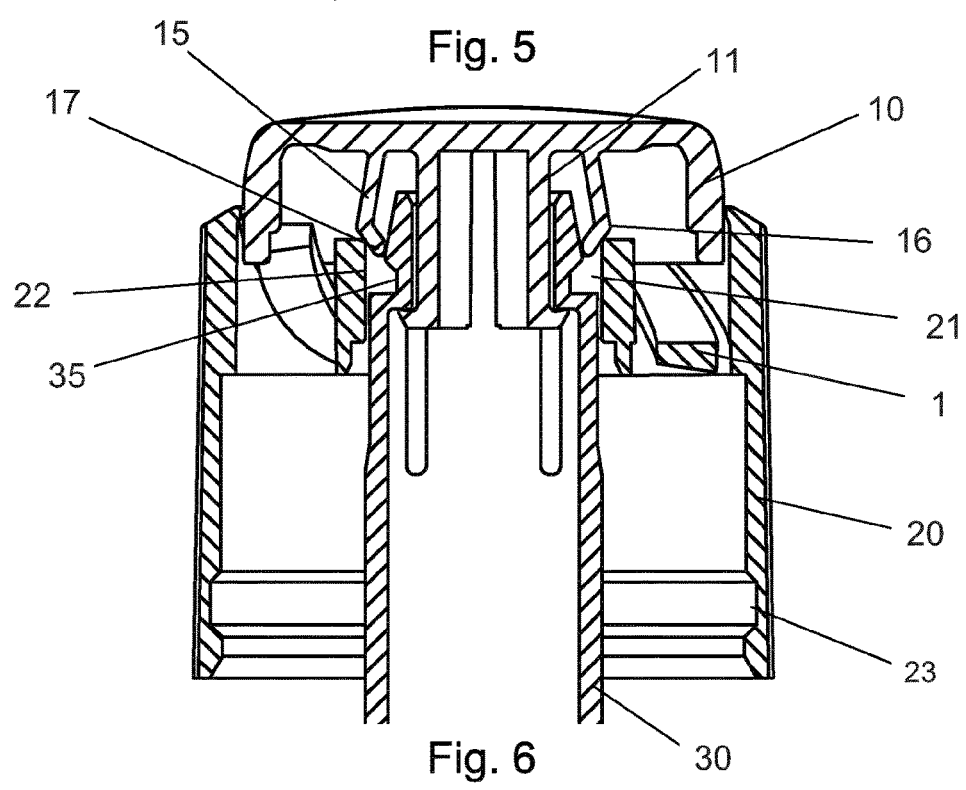
FIG. 6 show a cross sectional view of a different embodiment.

The embodiment disclosed in FIG. 6 basically operates in the same way as the first embodiment. The injection button 10 is here further provided with a plurality of flexible arms 15 working as the fingers 31 of the previous embodiment. The arms 15 has an outer edge 16 defining a diameter greater than the internal diameter of the channel 21 such that the arms 15 is deflected inwardly when the outer edge 16 of the arms 15 come into contact with the inside wall 22 of the channel 21. When forced inwardly, an inwardly pointing part 17 of these arms 15 engages behind a ridge or track 35 in the release tube 30.

When the return spring 1 is released, the spring force will first move the injection button 10 together with the release tube 30 in the proximal direction until the drive member has reengaged the housing, where after the remaining spring force is used to only move the injection button 10 into its initial position.

In FIG. 6, the return spring 1 is depictured as a moulded polymeric spring element however it could easily be an ordinary metallic compression spring. It is notable that the return spring 1 need not be in physical abutment with the injection button 10, since due to the present invention, the initial movement of the return spring 1 upon release of the injection button 10 is transferred directly to lifting the release element 30.

Further, the dose setting button 20 as depictured in FIG. 6 is provided with an internal track 23 which engages a similar ridge (not shown) on the housing to rotatable couple the dose setting member 20 to the housing.

Some preferred embodiments have been shown in the foregoing, but it should be stressed that the invention is not limited to these, but may be embodied in other ways within the subject matter defined in the following claims

The invention claimed is:

1. A spring-loaded medical injection device for automatically ejecting set doses of a drug having an injection button movable in a distal direction against the bias of a return spring, and movable proximally by the force of the return spring, and further comprising;

a housing having a proximal end carrying the injection button, a rotatable dose setting member coupled to the housing for straining an injection spring when setting the size of the dose to be injected, an axially movable release element for releasing the strained injection spring to drive a driver thereby ejecting the set dose, which release element is axially movable from a first position to a second position by the injection button and movable from the second position back to the first position by the force of the return spring, a plurality of radially movable fingers which releasably couples the injection button and the release element and which fingers are provided either integral with the injection button or integral with the release element, and;

which fingers in the first position are in a radially disengaged position wherein the injection button is disengaged from the release element allowing the injection button to move axially independently of the release element, and which fingers in the second position are in a radially engaging position wherein the injection button engages with the release element such that the injection button moves axially together with the release element.

2. A spring-loaded medical injection device for automatically ejecting set doses according to claim 1, wherein at least a part of the release element and a part of the injection button is axially guided in a channel having an internal diameter.

3. A spring-loaded medical injection device for automatically ejecting set doses according to claim 2, wherein the channel is provided in the dose setting member or in the housing.

4. A spring-loaded medical injection device for automatically ejecting set doses according to claim 2, wherein a radially outer edge of the plurality of fingers defines a diameter greater that the internal diameter of the channel.

5. A spring-loaded medical injection device for automatically ejecting set doses according to claim 2, wherein the plurality of fingers are provided integral with the release element.

6. A spring-loaded medical injection device for automatically ejecting set doses according to claim 5, wherein the fingers are provided with inwardly pointing structures engaging behind a ridge provided on the injection button in the engaged position of the fingers.

7. A spring-loaded medical injection device for automatically ejecting set doses according to claim 2, wherein the plurality of fingers are provided integral with the injection button.

8. A spring-loaded medical injection device for automatically ejecting set doses according to claim 7, wherein the fingers are provided with inwardly pointing structures engaging behind a ridge or track provided on the release element in the engaged position of the fingers.

9. A spring-loaded medical injection device for automatically ejecting set doses according to claim 1, wherein the bias of the return spring urging the injection button in the proximal direction is a polymeric spring.

10. A spring-loaded medical injection device for automatically ejecting set doses according to claim 9, wherein the polymeric spring is moulded as an integral part of the dose setting member or as an integral part of the injection button.

* * * * *